United States Patent
Shkolnikov et al.

(10) Patent No.: US 11,198,841 B2
(45) Date of Patent: Dec. 14, 2021

(54) PORATED CELL EJECTION DEVICES

(71) Applicant: HEWLETT-PACKARD DEVELOPMENT COMPANY, L.P., Houston, TX (US)

(72) Inventors: Viktor Shkolnikov, Palo Alto, CA (US); Kenneth Ward, Corvallis, OR (US)

(73) Assignee: Hewlett-Packard Development Company, L.P., Spring, TX (US)

(*) Notice: Subject to any disclaimer, the term of this patent is extended or adjusted under 35 U.S.C. 154(b) by 670 days.

(21) Appl. No.: 16/076,545

(22) PCT Filed: Jun. 9, 2017

(86) PCT No.: PCT/US2017/036732
§ 371 (c)(1),
(2) Date: Aug. 8, 2018

(87) PCT Pub. No.: WO2018/226240
PCT Pub. Date: Dec. 13, 2018

(65) Prior Publication Data
US 2021/0179991 A1    Jun. 17, 2021

(51) Int. Cl.
*C12M 3/00* (2006.01)
*C12M 1/00* (2006.01)
*C12M 3/06* (2006.01)
*B01L 3/02* (2006.01)
*C12M 1/42* (2006.01)
*C12N 15/87* (2006.01)

(52) U.S. Cl.
CPC ........... *C12M 23/16* (2013.01); *B01L 3/0268* (2013.01); *C12M 23/40* (2013.01); *C12M 35/02* (2013.01); *C12N 15/87* (2013.01); *B01L 2200/0647* (2013.01); *B01L 2300/0645* (2013.01)

(58) Field of Classification Search
CPC ....... C12M 35/00; C12M 35/02; C12M 35/04
See application file for complete search history.

(56) References Cited

U.S. PATENT DOCUMENTS 5,098,843 A    3/1992  Calvin
5,134,070 A *  7/1992  Casnig .................. C12M 23/10
                                                   204/406

(Continued)

OTHER PUBLICATIONS

Garcia et al., "Microfluidic Screening of Electric Fields for Electroporation", Scientific Reports 6, Article No. 21238, Retrieved from Internet—https://www.nature.com/articles/srep21238, 2016, 20 Pages.

*Primary Examiner* — Nathan A Bowers
(74) *Attorney, Agent, or Firm* — Fabian VanCott

(57) ABSTRACT

A microfluidic device may include a microfluidic channel including an electrode placed at opposite ends of the microfluidic channel to create an electrical field within the channel and an ejection device to eject at least one cell porated within the electrical field. A cassette may include a substrate, a die coupled to the substrate, a microfluidic channel defined within the die, the microfluidic channel including a necked portion to receive a cell therein and at least two electrodes each placed at a first and a second end of the microfluidic channel to apply an electric field to the cell above a proration threshold and a cell ejection device to eject the cell from the die.

5 Claims, 7 Drawing Sheets

(56) References Cited

U.S. PATENT DOCUMENTS

| | | | |
|---|---|---|---|
| 6,355,485 B1 | 3/2002 | Jaroszeski et al. | |
| 6,653,136 B1 | 11/2003 | Dodgson et al. | |
| 9,535,000 B2 | 1/2017 | Sadri et al. | |
| 10,307,783 B1* | 6/2019 | Gruenbacher | B05B 17/00 |
| 2002/0187503 A1* | 12/2002 | Harrold | B01L 3/502746 |
| | | | 435/6.12 |
| 2008/0286751 A1 | 11/2008 | Renaud et al. | |
| 2009/0294290 A1 | 12/2009 | Furusawa et al. | |
| 2011/0213288 A1* | 9/2011 | Choi | C12N 15/87 |
| | | | 604/6.08 |
| 2012/0276635 A1 | 11/2012 | Lu et al. | |
| 2013/0083127 A1* | 4/2013 | Kim | B01L 9/547 |
| | | | 347/47 |
| 2014/0113356 A1 | 4/2014 | Tseng et al. | |
| 2014/0220665 A1* | 8/2014 | King | C12M 35/02 |
| | | | 435/283.1 |
| 2016/0115470 A1 | 4/2016 | Cho et al. | |
| 2017/0059590 A1* | 3/2017 | McPeak | G01N 1/4077 |

* cited by examiner

PORATED CELL EJECTION DEVICES

BACKGROUND

Transfection of cells is the introduction of nucleic acids such as deoxyribonucleic acid (DNA), proteins, and/or other molecules into a cell. This may be done to alter the genetic identity of the cell or otherwise change the behavior of the cell. This allows, in an example, the production of genetically modified organisms that may be used in scientific research, medications, or food industry related endeavors.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
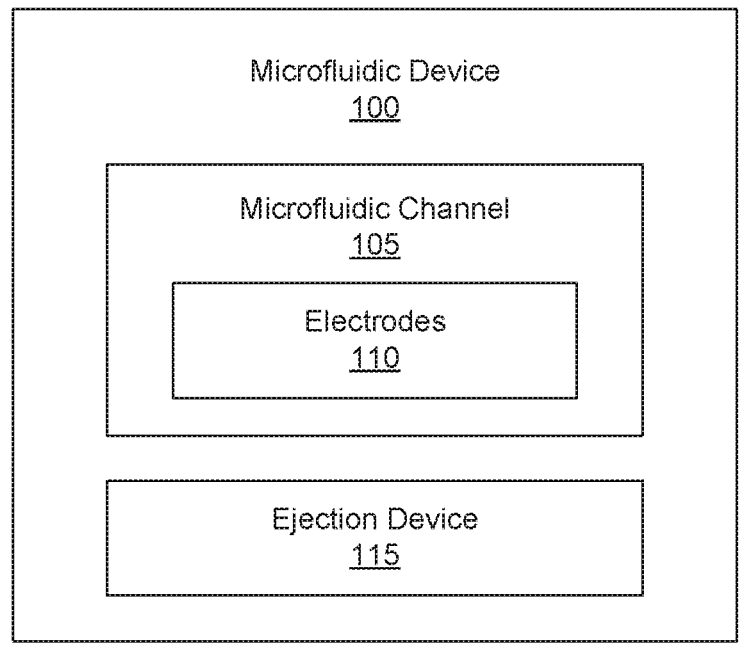
FIG. 1 is a diagram of a microfluidic device according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

As described above, transfection processes allow for the introduction of molecules into a cell membrane in an attempt to alter the performance, behavior, and/or attributes of the cell. Transfection may be accomplished via three different methods: viral, lipofection, and electrotransfection (i.e., transfection via electroporation). Viral transfection includes the use of a virus to introduce the molecule into the cell membrane. The virus may have the molecule coupled to it and, as the virus attacks the cell, the molecule is injected into the cell. However, viral transfection may be relatively laborious in comparison to other transfection methods and may have the additional potential of introduction of unwanted viral components into the cell itself.

Lipofection is a method that uses liposomes to introduce the molecules through the cell membrane. The liposomes may be made of, for example, phospholipid bilayer that easily merge with the membrane of the cell. However, similar to viral transfection, lipofection may be relatively more laborious in comparison to other transfection method and may also introduces surfactants into the cell membrane during the process.

Electrotransfection, transfection via electroporation, is the process of using an electric field to cause pores to form in the surface of the cell membrane allowing, for a period of time, certain molecules or other materials to pass into the cell. Currently electrotransfection is also a laborious process to optimize but often delivers the highest yield of nucleic acid material or other molecules into the cell. Currently, however, during the electrotransfection process, a user will to manually place the cells into a transfection chamber and remove them, batch-by-batch, rendering the process relatively labor intensive to explore a large space of transfection conditions. Additionally, separation of a cell among a number of cells individually in order to complete the transfection process after the poration process may be additionally laborious. Failure to properly single out a cell may limit the type of molecule or other substance transfected into the cell membrane to a single substance thereby limiting the different types of plasmids created during the transfection process.

The present specification describes a microfluidic device that includes a microfluidic channel including an electrode placed at opposite ends of the microfluidic channel to create an electrical field within the channel and an ejection device to eject at least one cell porated within the electrical field.

The present specification further describes a cassette that includes a substrate, a die coupled to the substrate, a microfluidic channel defined within the die, the microfluidic channel including a necked portion to receive a cell therein and at least two electrodes each placed at a first and a second end of the microfluidic channel to apply an electric field to the cell above a proration threshold and a cell ejection device to eject the cell from the die.

The present specification further describes a system for ejecting a fluid into an assay including an electrical dispensing device and a cassette comprising at least one dispense head, the at least one dispense head to eject at least one cell therefrom, the dispense head including a microfluidic channel having an electrode placed at opposite ends of the microfluidic channel to direct an electrical field toward the cell to cause poration to occur on the cell.

As used in the present specification and in the appended claims, the term "poration" is meant to be understood as a process of creating pores within a membrane of a cell. In an example, the poration process is completed by passing a cell through an electric field.

Further, as used in the present specification and in the appended claims the term "transfection" is meant to be understood as a process of introducing a particle through the membrane of a cell. Still further, the term "particle" is meant to be understood as any element that could be introduced into a cell through the membrane of the cell.

Additionally, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may or may not be included in other examples.

Turning now to the figures, FIG. 1 is a diagram of a microfluidic device (100) according to an example of the principles described herein. In an example, the microfluidic device (100) may include a microfluidic channel (105) having at least two electrodes (110) placed at opposite ends of the microfluidic channel (105) and an ejection device (115).

In an example, the microfluidic channel (105) may include a narrowed portion placed between the electrodes (110). In an example, the microfluidic channel (105) allows a number of cells to pass therethrough and may be forced to pass through the narrowed portion of the microfluidic channel (105). This may cause the cells to pass through the narrow portion at a cell by cell basis or at least in a single file manner.

As the cells pass through the narrowed portion of the microfluidic channel (105), one of the electrodes (110) placed at one end of the microfluidic channel (105) may be arranged such that an electrical field is directed toward the narrowed portion of the microfluidic channel (105). Another electrode (110) may be placed at a second end of the microfluidic channel (105) with that electrode (110) also being arranged to direct an electric field toward the narrow portion of the microfluidic channel (105). With both of the electrodes (110) arranged to direct an electric field towards the narrow portion of the microfluidic channel (105), a generally uniform electrical field may be realized within, at least, the narrow portion of the microfluidic channel (105). In an example, the electrodes (110) may implement a voltage that applies an electric field across the narrow portion of the microfluidic channel (105) based on the type of cell being passed through the microfluidic channel (105).

In an example, the electrodes (110) on a single end of the microfluidic channel (105) may be the electrodes (110) activated. In this example, a gradient electrical field may be produced within the narrow portion of the microfluidic channel (105). Further, the gradient electrical field produced by the electrodes (110) on the single end of the microfluidic channel (105) allows the cell to gradually come into a relatively higher electric field regions. By doing so, the reproducibility of any transfection process may be increased because the reproducibility of the electric field used to porate the cell will be present. Indeed, there would be a point within the spectrum of the electric field created by the electrodes (110) on the single end of the microfluidic channel (105) where each of the cells will undergo the poration process. Where the poration process is consistently reproducible, the reproducibility of the transfection will be relatively more likely.

When the electric field is applied to any cell, the cells become porated. Specifically, transient poration of the membrane of the cell is achieved as the cell passes through the narrow portion of the microfluidic channel (105) where the electric field is concentrated using the electrodes (110). The intensity of the electric field, and in turn the voltage used to create the electric field, may be varied depending on the type of cell to be porated, the length of the narrow portion of the microfluidic channel (105), the width of the microfluidic channel (105), and the solution used to carry the cells through the microfluidic channel (105), among other characteristics of the system. The present specification, therefore, contemplates a microfluidic device (100) that may apply an adjustable amount of voltage to the electrodes (110) in order to achieve a relatively higher transfection rate than would otherwise be accomplished using the other transfection methods described herein.

The electrodes (110) may be made of any conductive material that can direct an electrical field within the microfluidic channel (105) as described herein. As will be described in more detail herein, the electrodes (110) may have a voltage supplied to them via a number of electrical traces formed within and/or on the microfluidic device. These electrical traces may be selectively electrically coupled to an electrical dispensing device that may carry the microfluidic device (100) over a well plate to dispense at least one cell from the microfluidic device (100). The electrical dispensing device may be the source of the voltage used by the microfluidic device (100) to, at least, create the electrical field in the narrow portion of the microfluidic channel (105).

The ejection of the cell from the microfluidic device (100) may be accomplished using an ejection device (115) placed downstream of the microfluidic channel (105). The ejection device (115) may be a piezoelectric device that, when an electric charge is applied to it, causes the at least one cell to be ejected out of the microfluidic device (100). Alternative ejection devices may also be used such as a thermal excitation device and the present specification contemplates the use of such alternative ejection devices. Similar to the electrodes (110) described herein, an electronic dispensing device may be provided as the voltage source for the activation of the ejection device (115).

In an example, the ejection device (115) may include a detector that detects the presence of at least one cell within a firing chamber housing the ejection device (115). In an example, the ejection device (115) may include a detector that detects the type of cell within the firing chamber. These detectors may be used to allow the microfluidic device (100) to eject a single cell from the microfluidic device (100) and into an individual well of a well plate. In an example, this allows for the porated cells to be individually ejected into wells defined within a well plate or into a disposal location such as a spittoon.

In an example, any transfection elements such as DNA, proteins, antibodies, among others, may be provided in a transfection reservoir of the microfluidic device (100). In this example, the transfection elements may be circulated through the narrow portion of the microfluidic channel (105) and/or within other microfluidic channels/reservoirs within the microfluidic device (100) in order to complete the transfection process.

In an example, the microfluidic device (100) may be completely devoid of any transfection elements or transfection reservoir. In this example, a single cell may be ejected into a well of a well plate where a predetermined transfection element is kept. The ejection of the porated cell by the ejection device (115) ejects the single cell before the pores created in the membrane of the cell close up. In some instances, the pores may close within 15 to 45 minutes of poration by the electrodes (110).

Figure 2:
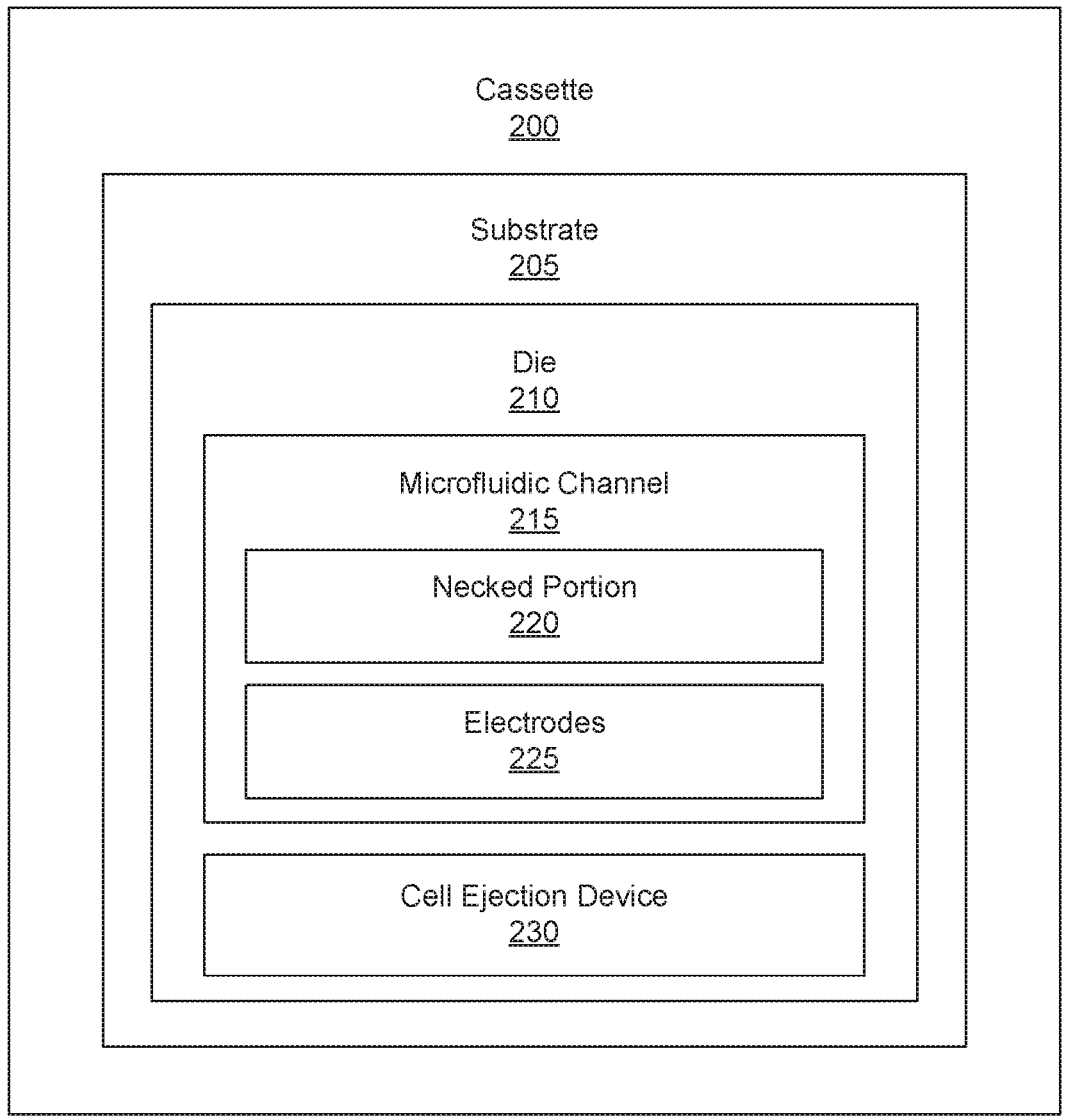
FIG. 2 is a block diagram of cassette according to an example of the principles described herein.

FIG. 2 is a block diagram of cassette (200) according to an example of the principles described herein. The cassette (200) may include a substrate (205) with a die (210) coupled thereto. The die (210) itself may include at least one microfluidic channel (215) have a necked portion (220) and a plurality of electrodes (225) placed at opposite ends of the microfluidic channel (215). The die (210) may further include a cell ejection device (230) used to eject at least one cell from the die (210) and cassette (200).

In an example, the substrate (205) may be made of any resilient material that allows the cassette (200) to interface with an automated ejection system. In an example, the substrate (205) is made of a plastic. In an example, the substrate (205) is made of polyether ether ketone (PEEK). In an example, the substrate (205) is made of polyetherimide (PEI).

The die (210) may be any device used eject any object and/or fluid from the cassette (200). In an example, the die (210) is a silicon die. In an example, the die (210) may include any number of layers of any type of material. In an example, the die (210) may include a silicon substrate having a rear face of the silicon die being exposed to atmosphere via a slot defined in the substrate (205) and a reservoir also defined in the substrate (205). A number of cells, for example, to be ejected from the die (210) may be placed in the reservoir and, via the slot, may be provided to the die (210) for ejection of the cells. In an example, the die (210) may further include a nozzle plate layer that includes a number of nozzles through which the cells are ejected.

Similar to the microfluidic channel (FIG. 1, 105) of FIG. 1, the microfluidic channel (215) may include a narrowed portion placed between the electrodes (225). In an example, the microfluidic channel (215) allows a number of cells to pass therethrough. As the cells pass through the narrowed portion of the microfluidic channel (215), one of the electrodes (225) placed at one end of the microfluidic channel (215) may direct an electrical field toward the narrowed portion of the microfluidic channel (215). Another electrode (225) may be placed at a second end of the microfluidic channel (215) with that electrode (225) also directing an electric field toward the narrow portion of the microfluidic channel (215). With both of the electrodes (225) directing an electric field towards the narrow portion of the microfluidic channel (215), a generally uniform electrical field may be realized within, at least, the narrow portion of the microfluidic channel (215).

In an example; transient poration of the membrane of the cell is achieved as the cell passes through the narrow portion of the microfluidic channel (215) where the electric field is concentrated using the electrodes (225). The intensity of the electric field, and in turn the voltage used to create the electric field, may be varied depending on the type of cell to be porated, the length of the narrow portion of the microfluidic channel (215), the width of the microfluidic channel (215), and the solution used to carry the cells through the microfluidic channel (215), among other characteristics of the system. The present specification, therefore, contemplates a cassette (200) that may apply an adjustable amount of voltage to the electrodes (225) in order to achieve a relatively higher transfection rate than would otherwise be accomplished using the other transfection methods described herein.

Again, the electrodes (225) may be made of any conductive material that can be used to create an electrical field within the microfluidic channel (215) as described herein. The electrodes (225) may have a voltage supplied to them via a number of electrical traces formed within and/or on the cassette (200). These electrical traces may be selectively electrically coupled to an electrical dispensing device that may carry the cassette (200) over a well plate to dispense at least one cell from the die (210) coupled to the cassette (200). The electrical dispensing device may be the source of the voltage used by the cassette (200) to, at least, create the electrical field in the narrow portion of the microfluidic channel (215).

The ejection of the cell from the cassette (200) may be accomplished using a cell ejection device (230) placed downstream of the microfluidic channel (215). The cell ejection device (230) may be a piezoelectric device that, when an electric charge is applied to it, causes the at least one cell to be ejected out of the cassette (200). Alternative ejection devices may also be used such as a thermal excitation device and the present specification contemplates the use of such alternative ejection devices. Similar to the electrodes (225) described herein, an electronic dispensing device may be provided as the voltage source for the activation of the cell ejection device (230).

In an example, the various microfluidic channels (215) defined in the die (210) of the cassette (200) may include any number of additional sensors used to detect the presence of a cell or a type of cell. Specifically, the cassette (200) may be controlled by an electrical dispensing device to eject a cell or certain type of cell from the die (210) following the poration process accomplished by the electrodes (225). The sensors may be any type of sensor that can detect any cell or type of cell within any cavity of the die (210) such that ejection of the cell may be selective. In an example, the electrical dispensing device may send signals to the cassette (200) to eject a certain type of cell into a well of a well plate after the sensors have determined the presence of cell and/or the presence of a specific type of cell. Although the sensors may be included in any location within the die (210) of the cassette (200), in an example these sensors may be included in a firing chamber located at or near the cell ejection device (230). This allows for immediate ejection of the cell into a well after the cell has been porated. In an example, a cell that is not to be ejected into a well of the well plate may, instead, be ejected into a spittoon located by or on the well plate. This spittoon may hold those cells that are not to be included with the cells undergoing the herein described transfection process.

In an example, any transfection elements such as DNA, proteins, antibodies, among others, may be provided in a transfection reservoir of the cassette (200). In this example, the transfection elements may be circulated through the narrow portion of the microfluidic channel (215) and/or within other microfluidic channels/reservoirs within the cassette (200) in order to complete the transfection process.

In an example, the cassette (200) may be completely devoid of any transfection elements or transfection reservoir. In this example, a single cell may be ejected into a well of a well plate where a predetermined transfection element is kept. The ejection of the porated cell by the cell ejection device (230) occurs before the pores created in the membrane of the cell close up. In some instances, the pores may close within 15 to 45 minutes of poration by the electrodes (225).

Figure 3:
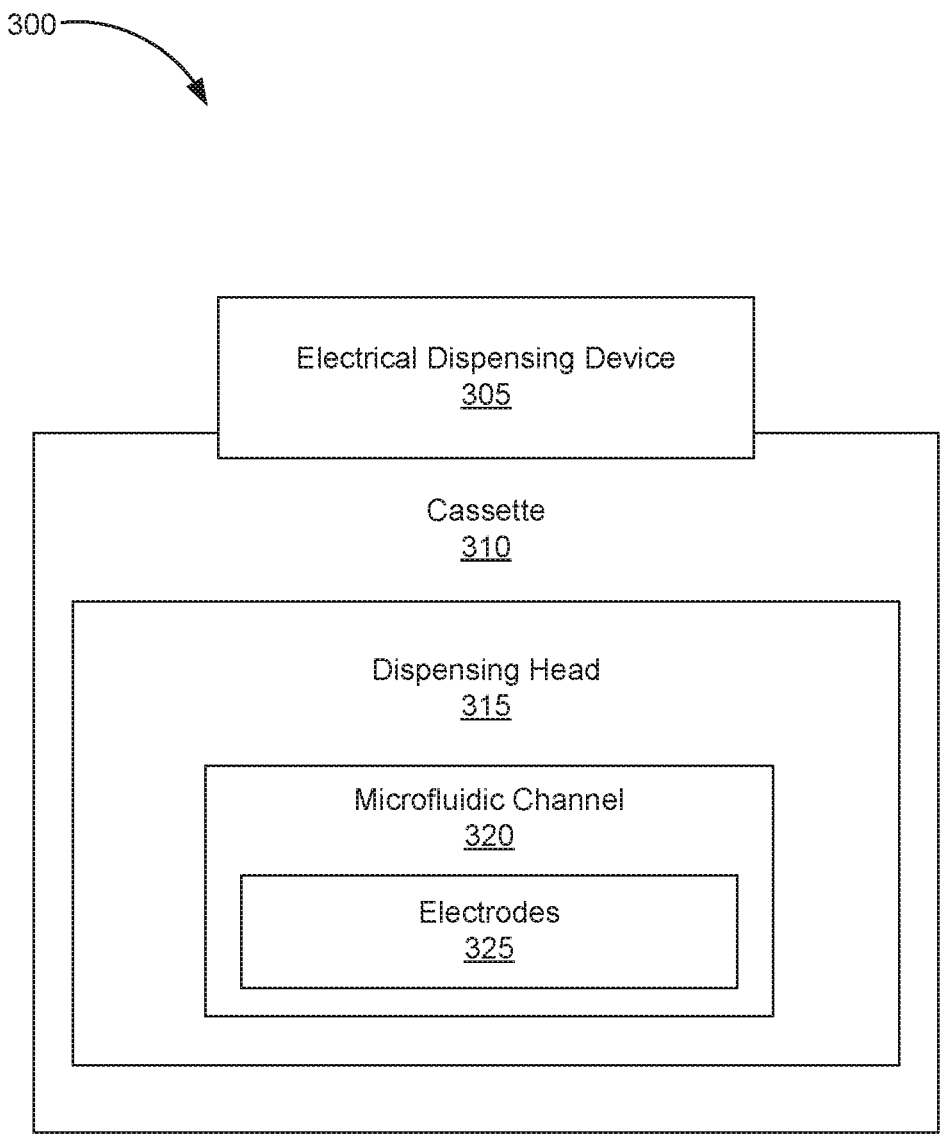
FIG. 3 is a block diagram of a cell ejection system according to an example of the principles described herein.

FIG. 3 is a block diagram of a cell ejection system (300) according to an example of the principles described herein. The cell ejection system (300) may include a cassette (310) and an electrical dispensing device (305). The cassette (310) may include a dispensing head (315) that has at least one microfluidic channel (320) defined therein with a plurality of electrodes (325) placed along a portion of the microfluidic channel (320). The cassette (310) may similar to the cassette (FIG. 2, 200) as described in connection with FIG. 2.

In an example, the cassette (310) includes a number of electrical leads leading from the dispensing head (315) to a number of electrically conductive pads defined on at least one surface of the cassette (310). The pads may allow the cassette (310) to interface, electrically, with the electrical dispensing device (305) in order to, at least, provide a voltage to the electrodes (325) defined in the dispensing head (315) and cause the cassette (310) to be moved along a surface of the well plate.

In an example, the electrical dispensing device (305) may include a printed circuit assembly (PCA) that electrically interfaces with the pads and electrical traces defined on the cassette (310). With this interface, the electrodes (325), at least, will be coupled to a voltage supply of the electrical dispensing device (305). Further, when the cassette (310) is, selectively; electrically and physically coupled to the electrical dispensing device (305), the electrical dispensing device (305) may cause at least the dispensing head (315) to be moved over any well defined in a well plate underneath the cassette (310) so that a cell may be ejected from the dispensing head (315) as described herein. This may allow each or a number of wells of the well plate to receive a cell or a number of cells so that the transfected or to be transfected cells can be maintained. Thus, the cell ejection system (300) may be used to transfect minute quantities of cells in minute volumes of fluids. This may save on the cost of the transfection materials introduced into the cells during the transfection process as well as allow for specific cells to be examined after such a process. Further, with a well plate having a plurality of wells defined therein, each well may maintain an amount of transfection material different from all other wells of the well plate. This may allow multiple types of transfections to occur with the use of a single well plate.

The dispensing head (315) may be similar to the die (FIG. 2, 210) and ejection device (FIG. 1, 115) of FIGS. 2 and 1 respectively. Particularly, the dispensing head (315) may include a silicon substrate having a rear face of the silicon die being exposed to atmosphere via a slot defined in a substrate similar to the subject (FIG. 2, 205) of FIG. 2. A reservoir may also be defined in the substrate to hold a number of cells, for example. These cells may be ejected from the dispensing head (315) and may be retained in the reservoir until such ejection. The cells may be provided to the dispensing head (315) via a slot defined in the substrate. In an example, the dispensing head (315) may further include a nozzle plate layer that includes a number of nozzles through which the cells are ejected.

The microfluidic channel (320) and its associated electrodes (325) may be similar to the electrodes and microfluidic channels described in connection with FIGS. 1 and 2.

Figure 4A:
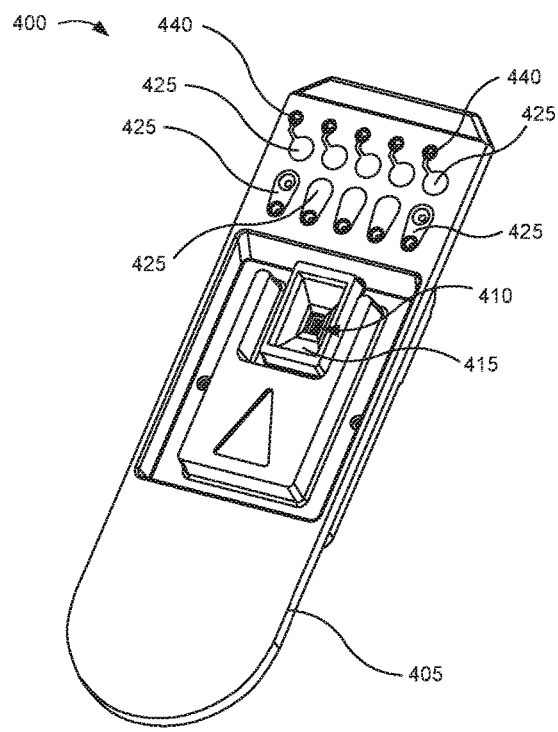
FIGS. 4A and 4B are perspective top and bottom views, respectively, of a cassette according to an example of the principles described herein.
Figure 4B:
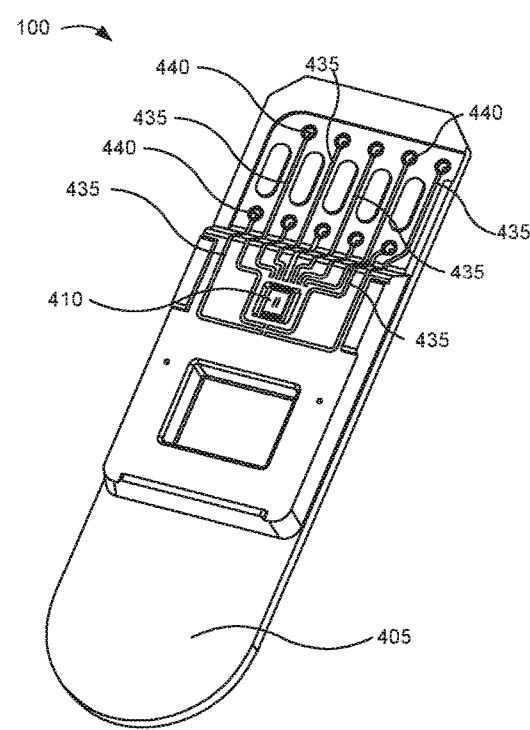

FIGS. 4A and 4B are perspective top and bottom views, respectively, of a cassette (400) according to an example of the principles described herein. FIGS. 4A and 4B is meant to be understood as an example and the present specification contemplates the use of other forms of cassettes (400) that achieve similar functions described herein.

As described herein, the cassette (400) includes a substrate (405), a die (410) coupled to the substrate (405), and a reservoir (415) defined in the substrate (405). The cassette (400) with its substrate (405), die (410), and reservoir (415) may be similar to the cassette (FIG. 2, 200; FIG. 3, 310) as described in connection with FIGS. 2, and 3.

The substrate (405) may be formed to allow a user to insert or otherwise interface the cassette (400) with a system for ejecting a fluid into an assay such as the electrical dispensing device (FIG. 3, 305) described herein. In the example show in FIGS. 4A and 4B, the substrate (405) may include a handle. The handle allows a user to grip the cassette (400) in order to manipulate the cassette (400) and place the cassette (400) into the system used to eject a fluid or object such as a cell into a well plate.

The cassette (400) may further include a number of connection pads (425) and electrical traces (430) so that the die (410) of the cassette (400) can receive electrical signals directing when, where, and how to eject a cell therefrom. In an example, the cassette (400) is moved relative to a well plate positioned below the cassette (400) such that placement of the die (410) over any portion of the well plate and ejection of the cell from the die (410) allows at least one cell to be ejected into any number of wells formed in the well plate. The ejection of the cell from the die (410) is directed by a controller of, for example the electrical dispensing device as described herein.

Thus, in order to allow the cassette (400) to interface with the system for ejecting a cell into a well plate, the cassette (400) may include a number of contact pads (425) that interface with, for example, a number of pogo connectors on a printed circuit assembly (PCA) of the electrical dispensing device. In the examples shown in the figures of the present specification, the number of contact pads (425) is ten. However, the present specification contemplates the use of less or more contact pads (425). The number of contact pads (425) may be varied among different examples because the die (410) may receive signals from the PCA directing a number of microelectromechanical systems (MEMS) devices to be activated.

Consequently, more or less contact pads (425) may be added or subtracted from those shown in FIGS. 4A and 4B based on the number of signals used to activate any number of MEMS devices within the die (410). Not all of the contact pads (425) have been indicated in FIGS. 4A and 4B in order to allow for better understanding of the cassette (400).

In an example, a number of traces (435) may electrically couple each of the contact pads (425) to a via (440). In other examples the contact pads (425) themselves may be electrically coupled to their respective vias (440) without the use of traces (435).

In an example, the contact pads (425) and traces (435) may be formed onto the surface of the substrate (405) using a laser direct structuring (LDS) process. During the LDS process, the non-conductive, metallic, inorganic compounds are activated by a laser providing a surface into which a layer of conduct metal may be deposited using, for example, an electroless copper bath. The vias (440) may provide an electrical connection to a number of other traces (435) formed on an opposite side of the cassette (400).

FIG. 4B is a back, perspective view of the cassette (400) of FIG. 4A according to an example of the principles described herein. The vias (440) provide an electrical connection between the contact pads (425) on the front side of the cassette (400) to a number of traces (435) defined on the back side of the cassette (400). These traces (435) electrically couple each of the vias (440) to at least one die pad defined on the die (410). In this manner, a PCA may interface with the contact pads (425) defined on the front of the cassette (400) in order to send electrical signals to the die (410) to cause the die (410) to, at least, eject at least one cell therefrom.

As described herein, the cassette (400) of FIGS. 4A and 4B includes a reservoir (415). The reservoir (415), in this example, may generally be in the form of a funnel shape such that a user, during operation, may provide at least one cell therein. In an example, the at least one cell is provided via a blood sample being placed in the reservoir (415). The funnel shape of the reservoir (415) may funnel the sample to a slot defined above a proximal side of the die (410). Thus, the funnel shaped reservoir (415) as shown in FIG. 4A may provide a constant supply of fluid and or cells to the die (410) using gravitational forces. As described above, additional reservoirs may be formed into the substrate (405) to hold an amount of transfection fluid or material. In this example, the transfection fluid or material may be provided to the die (410) similar to the at least one cell and may be mixed with the at least one cell before, during, or after the poration process engaged in by the electrodes (FIG. 3, 325) defined in the die (410).

Figure 5:
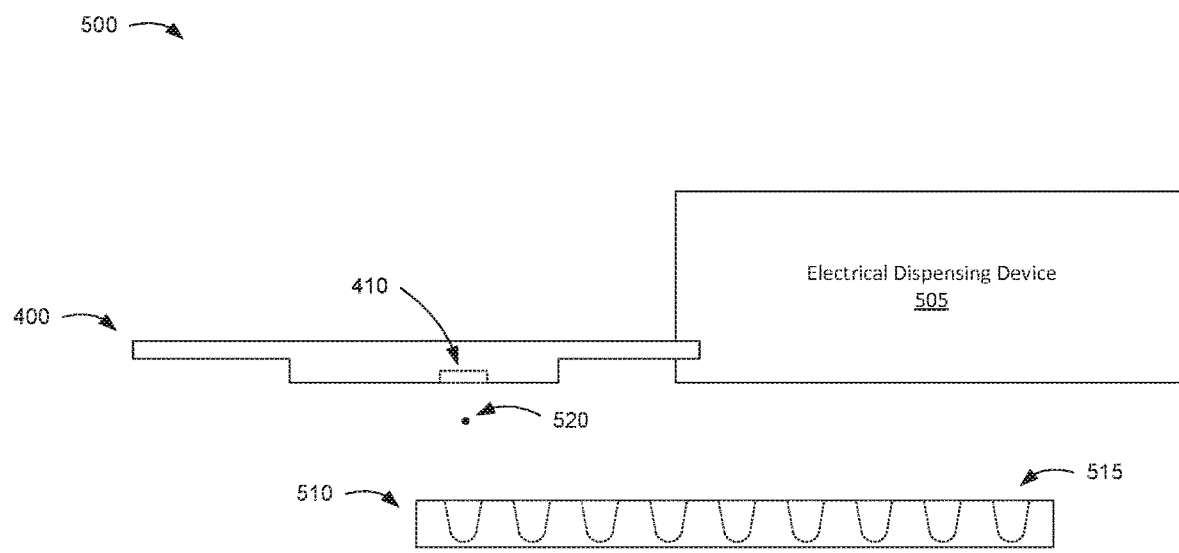
FIG. 5 is a block diagram of a cell ejection system according to an example of the principles described herein.

FIG. 5 is a block diagram of a cell ejection system (500) according to an example of the principles described herein. The cell ejection system (500) shows an electrical dispensing device (505) that carries a cassette (400) over and above a well plate (510). The cell ejection system (500) may direct a die (410) coupled to the cassette (400) when and where to eject a cell (520) into an individual well (515) of the well plate (510).

Figure 6:
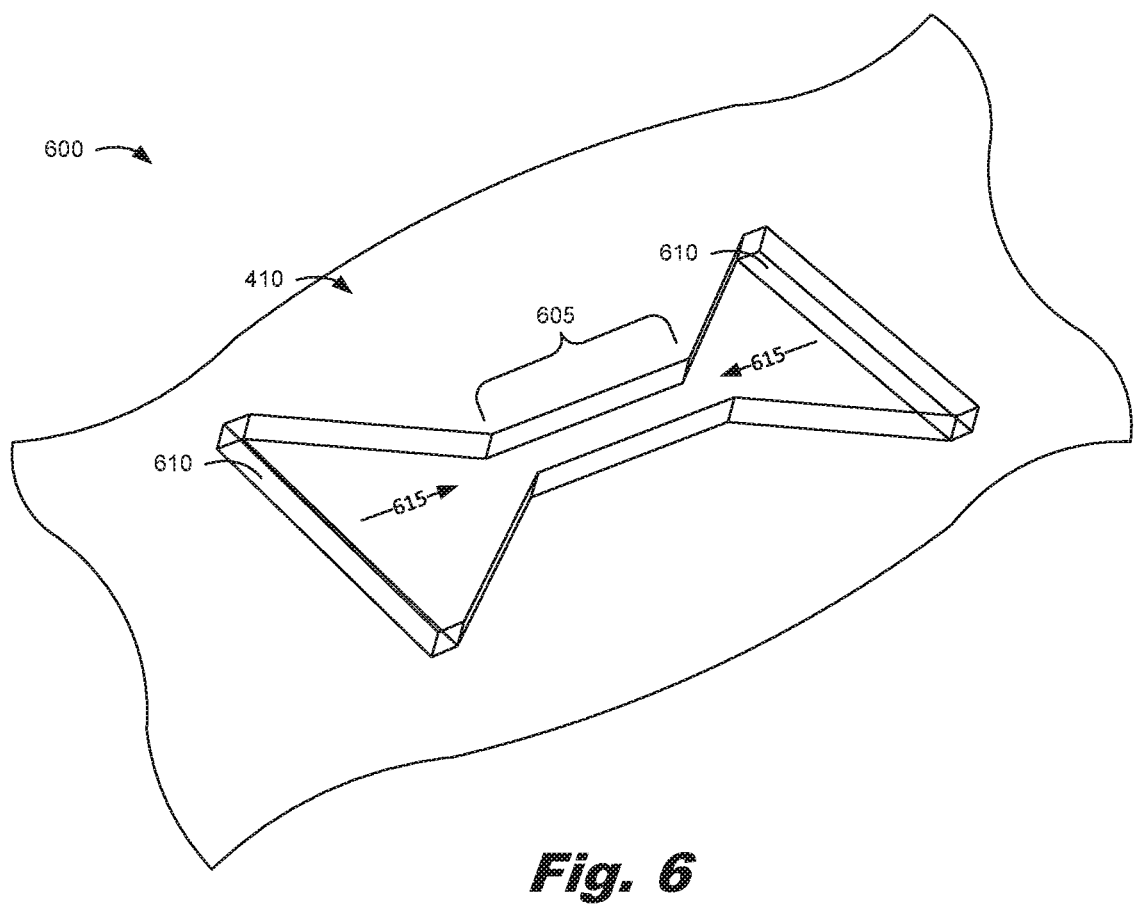
FIG. 6 is a perspective view of a microfluidic channel according to an example of the principles described herein.

FIG. 6 is a perspective view of a microfluidic channel (600) according to an example of the principles described herein. As described herein, the microfluidic channel (600) includes a narrowed portion (605) along the length of the microfluidic channel (600). Additionally, at least one electrode (610) may be placed at opposite ends of the microfluidic channel (600). The microfluidic channel (600) may be defined in the body of the die (410).

The electrodes (610) may cause an electric field to be produced at or near the narrowed portion (605). The electrical field may increase away from each of the electrodes (610) generally in the direction of arrows (615). In an example, one of the electrodes (610) placed at opposite ends of the microfluidic channel (600) may be activated in order to produce a gradiently increasing electrical field at or along the narrowed portion (605) of the microfluidic channel (600).

The dimensions of the narrowed portion (605) of the microfluidic channel (600) may be varied based on the type of cell to be porated by the electrodes (610). In an example, the length of the narrowed portion (605) may be between 50 and 130 μm. In an example, the length of the narrowed portion (605) may be between 60 and 120 μm. In an example, the width of the narrowed portion (605) may be between 5 and 35 μm. In an example, the width of the narrowed portion (605) may be between 15 and 30 μm. In an example, a maximum width of the microfluidic channel (600) may be between 140 and 160 μm. In an example, a maximum width of the microfluidic channel (600) may be 150 μm. In an example the distance between an end of the narrowed portion (605) of the microfluidic channel (600) and the electrode (610) may be between 80 and 100 μm. In an example the distance between an end of the narrowed portion (605) of the microfluidic channel (600) and the electrode (610) may be 90 μm. In an example, the width of the electrode may be 15 μm.

Figure 7:
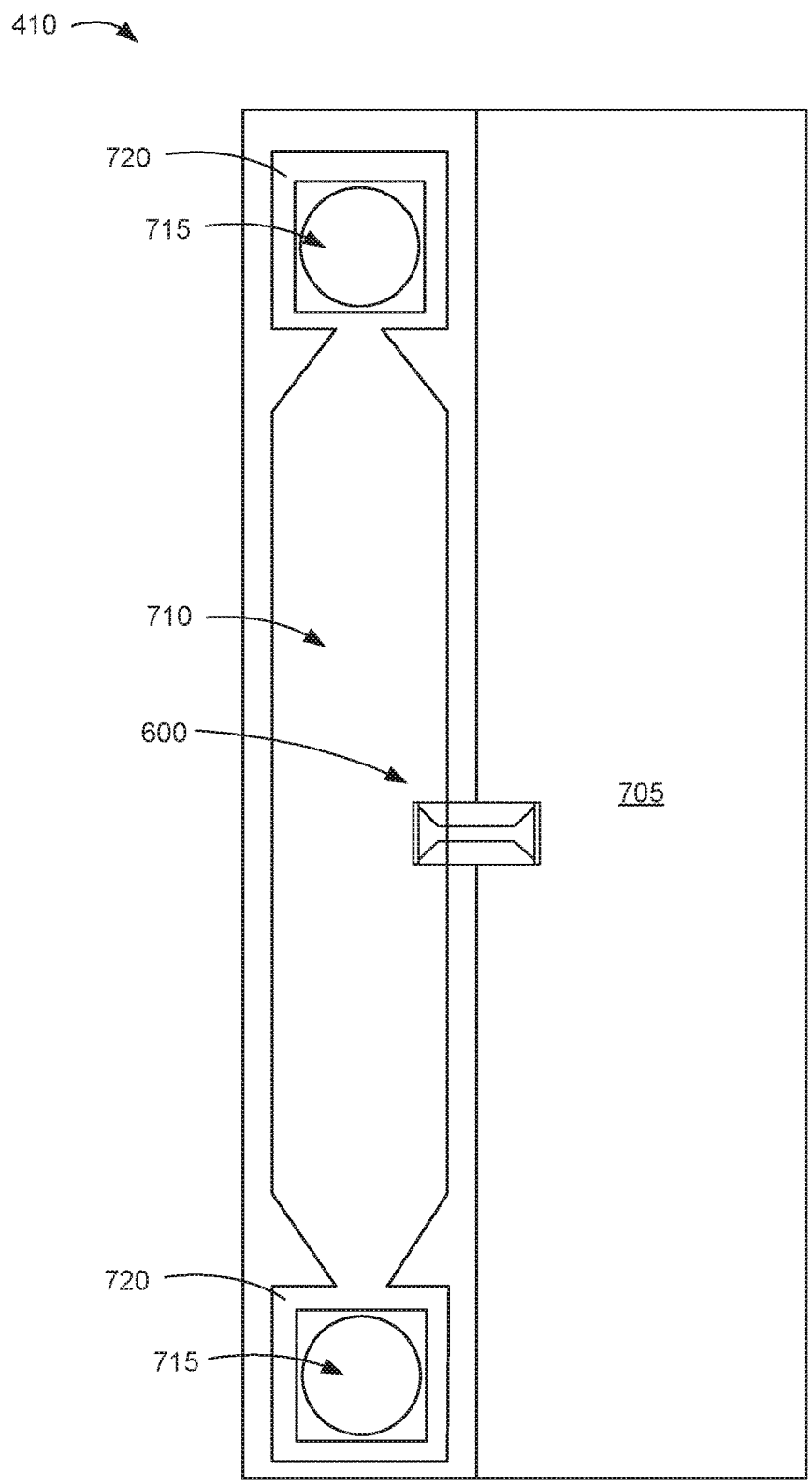
FIG. 7 is a block underside cutout view of the die of FIG. 4 according to an example, of the principles described herein.

FIG. 7 is a block underside cutout view of the die (410) of FIG. 4 according to an example, of the principles described herein. In FIG. 7, the gravitational force is applied out of the page when the cassette (FIG. 4, 400) housing the die (410) is coupled to the electrical dispensing device (FIG. 5, 505) as shown in FIG. 5.

The die (410) may have a first upstream portion (705) that may include any number of microfluidic channels, reservoirs, and/or pumps, among other microfluidic devices. In some examples, the cells may pass through or by a number of devices to prepare the cell for poration by the electrodes (610) and/or transport the cells through the narrowed portion (605) of the microfluidic channel (600). Once the cells have passed through the narrowed portion (605) they may be retained for some period of time in an accumulation area (710). The cells may then be directed towards a firing chamber (720) where an electrical dispensing device (715) ejects the cell out of the die (410); in the case of FIG. 7, in a direction out of the page.

Although FIG. 7 shows a single microfluidic channel (600), any number of microfluidic channels (600) may be bridged between the upstream portion (705) and the accumulation area (710). In this example, the plurality of microfluidic channels (600) may each porate different types of cells having, potentially, different dimensions and poratability properties.

The specification and figures describes a porated cell ejection device. The porated cell ejection device described herein allows a user to explore a relatively large poration parameter space during cell poration process so as to converge on an optimum transfection conditions for a variety of different types of cells. Additionally, the device and systems may achieve relatively higher transfection efficiency with respect to other types of poration and/or transfection devices. Still further, the cassettes, devices, and systems described herein may allow a user to replicate that level of transfection efficiency. The devices and systems also allow a user to explore a plurality of plasmids and/or cells with relatively less labor using other systems. Still further, the transfection of the porated cells produced by the electrodes in the microfluidic channel may be accomplished in minute quantities of fluids containing cells. Even still further, the ejection of the cells may be on a cell-by-cell basis thereby allowing a user to eject porated cells from the device into individual wells of a well plate; each well potentially maintaining a different type of transfection fluid or material.

The preceding description has been presented to illustrate and describe examples of the principles described. This description is not intended to be exhaustive or to limit these principles to any precise form disclosed. Many modifications and variations are possible in light of the above teaching.

What is claimed is:

1. A die for poration of cells, the die comprising:
    an upstream portion for containing cells to be porated;
    a microfluidic channel defined within the die, the microfluidic channel comprising:
        a necked portion to receive a cell therein; and
        electrodes placed at a first and a second end of the microfluidic channel to apply an electric field to the cell above a poration threshold;
    an accumulation area in which porated cells are retained prior to being ejected, the microfluidic channel communicating between the upstream portion and the accumulation area to deliver cells from the upstream portion to the accumulation area in a porated state; and
    two cell ejection devices to eject the cell from the die, the two cell ejection devices located at opposite ends of the accumulation area, each cell ejection device comprising a firing chamber with a thermal excitation device to eject a cell from the die.

2. The die of claim 1, further comprising multiple microfluidic channels communicating between the upstream portion and accumulation area, each microfluidic channel being differently structured to porate a different type of cell having different dimensions or poratability properties.

3. The die of claim 1, further comprising a transfection fluid reservoir to provide a transfection fluid to the cell within the die.

4. The die of claim 1, wherein the electrodes are arranged to produce a gradient electrical field in the microfluidic channel such that a cell gradually experiences higher electrical field regions when moving through the channel.

5. The die of claim 1, further comprising a detector to detect presence or type of a cell within the firing chamber of one of the cell ejection devices.

* * * * *